United States Patent
Lei et al.

(10) Patent No.: US 12,343,437 B2
(45) Date of Patent: Jul. 1, 2025

(54) LIGHT AND DISINFECTION SYSTEM AND A METHOD FOR DISINFECTING AN ILLUMINATED SURFACE BY THE SYSTEM

(71) Applicant: CONSUMER LIGHTING (U.S.), LLC, Norwalk, CT (US)

(72) Inventors: Ming Lei, Shanghai (CN); Huisheng Zhou, Shanghai (CN)

(73) Assignee: SAVANT TECHNOLOGIES LLC, East Cleveland, OH (US)

( * ) Notice: Subject to any disclaimer, the term of this patent is extended or adjusted under 35 U.S.C. 154(b) by 487 days.

(21) Appl. No.: 16/782,050

(22) Filed: Feb. 4, 2020

(65) Prior Publication Data
US 2020/0282089 A1 Sep. 10, 2020

(30) Foreign Application Priority Data
Feb. 14, 2019 (CN) .......................... 201910113788.X

(51) Int. Cl.
*A61L 2/10* (2006.01)
*A61L 2/24* (2006.01)
*H05B 47/13* (2020.01)

(52) U.S. Cl.
CPC ................ *A61L 2/10* (2013.01); *A61L 2/24* (2013.01); *H05B 47/13* (2020.01)

(58) Field of Classification Search
CPC .......... A61L 2/10; A61L 2/24; A61L 2202/11; A61L 2202/14; A61L 2/08; A61L 2202/25; H05B 47/13; H05B 47/115; Y02B 20/40
See application file for complete search history.

(56) References Cited

U.S. PATENT DOCUMENTS 7,635,203 B2 * 12/2009 Weaver, Jr. ............... F21K 9/64
362/241
10,767,846 B2 * 9/2020 Jiang ...................... H05B 45/37
(Continued)

FOREIGN PATENT DOCUMENTS

CN 201396611 Y 2/2010
CN 203395963 U 1/2014
(Continued)

OTHER PUBLICATIONS

Chinese First Office Action Received for Chinese Patent Application 201910113788.X mailed on Jan. 11, 2021, 14 pages (8 pages Official Copy + 6 pages English Translation).

*Primary Examiner* — Regina M Yoo
(74) *Attorney, Agent, or Firm* — WOOD IP LLC

(57) ABSTRACT

The present application discloses a light and disinfection system and a method for disinfecting an illuminated surface by the light and disinfection system, wherein the light and disinfection system comprises an illumination module, including an illumination source; a distance sensor for detecting a distance between the light and disinfection system and the illuminated surface; and a disinfection module, including a disinfection light source and a control unit, the control unit receiving the distance detected by the distance sensor and controlling an irradiation power of the disinfection light source based on the distance, such that an irradiation amount of the illuminated surface accumulated within one disinfection circle is kept at a predetermined value.

11 Claims, 4 Drawing Sheets

(56) References Cited

U.S. PATENT DOCUMENTS

| | | | | |
|---|---|---|---|---|
| 2011/0109235 A1* | 5/2011 | Link | .................. | H05B 45/46 |
| | | | | 315/191 |
| 2016/0025273 A1* | 1/2016 | van de Ven | .............. | F21K 9/23 |
| | | | | 362/293 |
| 2016/0106873 A1* | 4/2016 | Dobrinsky | ......... | G01N 21/6486 |
| | | | | 250/393 |
| 2017/0080117 A1* | 3/2017 | Gordon | .................. | A61L 2/10 |
| 2017/0296686 A1* | 10/2017 | Cole | .................. | A61L 2/24 |
| 2017/0321877 A1* | 11/2017 | Polidoro | .................. | A61L 9/20 |
| 2018/0003561 A1* | 1/2018 | Coombes | .............. | G01J 1/0403 |
| 2018/0110890 A1 | 4/2018 | Matsui | | |
| 2018/0193501 A1* | 7/2018 | Ufkes | .................. | A61L 2/10 |
| 2018/0311386 A1* | 11/2018 | Hawkins | .............. | H05B 47/19 |
| 2019/0022263 A1* | 1/2019 | Quilici | .................. | H05B 45/10 |
| 2019/0142981 A1* | 5/2019 | Kim | .................. | E03C 1/126 |
| | | | | 250/455.11 |

FOREIGN PATENT DOCUMENTS

| | | | | |
|---|---|---|---|---|
| CN | 107405415 A | 11/2017 | | |
| CN | 207298621 U | 5/2018 | | |
| WO | WO-2017083461 A1 * | 5/2017 | .............. | A61L 2/084 |

* cited by examiner

LIGHT AND DISINFECTION SYSTEM AND A METHOD FOR DISINFECTING AN ILLUMINATED SURFACE BY THE SYSTEM

FIELD

The present disclosure generally relates to a system and method for disinfection and sterilization using light, more specifically to a system and method for self-adaptive disinfection and sterilization on an illuminated surface.

BACKGROUND

It is found that ultraviolet, violet or blue light may have a function of disinfection and sterilization, such as inactivation of pathogen on an object surface, in the air or water. The pathogen refers to any microscopic organism that can cause disease or infection in human body, including bacteria, viruses, spores and fungi. Inactivation includes killing the pathogen, making it unable or impossible to reproduce, or making it unable to infect human. The ultraviolet (UV) refers to light having a wavelength in a range of 100 nm to 400 nm; four sub-ranges of the UV range comprises a vacuum UV ranging from 100 nm to 200 nm; UVC ranging from 200 nm to 280 nm; UVB ranging from 280 nm to 315 nm; and UVA ranging from 315 nm to 400 nm. The wavelength of the violet light is about 400 nm to about 450 nm, and the wavelength of the blue light is about 450 nm to about 490 nm.

In some known UV systems, UV light ranging from 200 nm to 300 nm, including some of the UVC range and UVB range, is utilized to destroy DNA or RNA of the pathogen so as to make its multiplication impossible, thus unable to infect human, achieving the goal of disinfection and sterilization. However, there exist some problems in these UV systems: firstly, irradiances of these UV systems are greater than 10 W/m2, and exposure to such UV lights may be harmful to human, particularly causing great damage to human's eyes; secondly, in order to achieve the goal of disinfection and sterilization, a surface to be disinfected needs to be illuminated by UV light for a long time, which cannot play the role of thorough sterilization if the time is too short, and which will accelerate degradation of the material performance of the surface to be disinfected, e.g., fading and the like, if the time is too long.

Therefore, it is desired to provide with a new light and disinfection system for solving at least one of the above problems.

SUMMARY

In one embodiment, the present application discloses a light and disinfection system, wherein the light and disinfection system comprises an illumination module, including an illumination source; a distance sensor for detecting a distance between the light and disinfection system and an illuminated surface; and a disinfection module, including a disinfection light source and a control unit, the control unit receiving the distance detected by the distance sensor and controlling an irradiation power of the disinfection light source based on the distance such that an irradiation amount of the illuminated surface accumulated within one disinfection circle is kept at a predetermined value.

In another embodiment, the present application discloses a method for disinfecting and sterilizing an illuminated surface by said light and disinfection system, the method comprising: detecting a distance between the light and disinfection system and the illuminated surface; and controlling an irradiation power of the disinfection light source in the light and disinfection system based on the distance, such that an irradiation amount of the illuminated surface accumulated within one disinfection circle is kept at a predetermined value.

BRIEF DESCRIPTION OF THE DRAWINGS

These and other features, aspects and advantages of the present application can be understood better in light of the following detailed description with reference to the accompanying drawings, in which similar reference signs represent similar components in the whole drawings, in which.

DETAILED DESCRIPTION

In order to help the person skilled in the art to exactly understand the subject matters claimed by the present invention, detailed description for embodiments of the present invention will be given with reference to the accompanying drawings in the following. In the following detailed description for those embodiments, some well-known functions or structures will not be described in details by the Description, to avoid disclosure of the present invention to be affected by unnecessary details.

Unless defined otherwise, the technical or scientific terms used in the Claims and the Description should have meanings as commonly understood by one of ordinary skilled in the art to which the present invention belongs. The terms "first", "second" and the like in the Description and the Claims do not mean any sequential order, quantity or importance, but are only used for distinguishing different components. The terms "a", "an" and the like do not denote a limitation of quantity, but denote the existence of at least one. Unless pointed out otherwise, terms such as "front", "rear", "lower" and/or "upper" and the like are used only for convenient explanation, rather than limiting to one position or one space orientation. "Or" and the like mean inclusive, and refer to one or all of the illustrated terms. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, but may comprise electric connection or coupling, no matter directly or indirectly.

Figure 1:
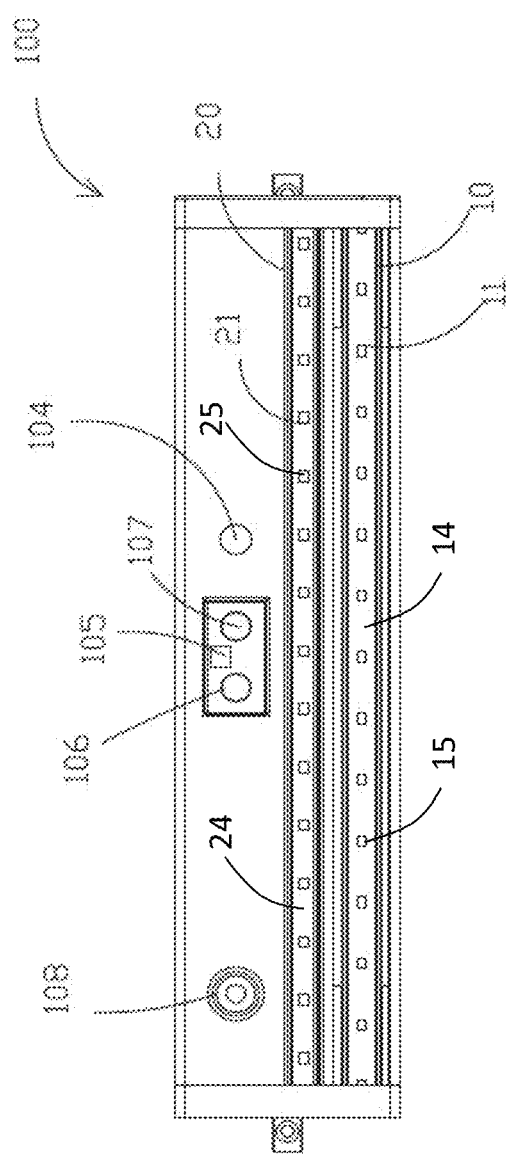
FIG. 1 is a front view of a light and disinfection system according to one embodiment of the present application.

As shown in FIG. 1, the present application reveals a light and disinfection system 100, comprising an illumination module 10 that includes an illumination source 11; a disinfection module 20 that includes a disinfection light source 21.

In some embodiments, the illumination source 11 comprises a white light source, e.g., white LED. In one embodiment, the disinfection light source 21 comprises a light source such as a UV light source, a violet light source or a blue light source, the UV light source including vacuum UV, UVC, UVB, UVA and the like. In some specific embodiments, the UV light source comprises a long-wavelength UV light source having a wavelength ranging from 280 nm to 380 nm. In some embodiments, the illumination module 10 and the disinfection module 20 may use a diffusion hood (not shown) for evenly diffusing the light produced by the light source. Specifically, the materials of the diffusion hoods used by the illumination module 10 and the disinfection module 20 may be the same, or may also be different, e.g., utilizing material such as quartz glass and the like to manufacture the diffusion hood of the UV light source, and utilizing PC, PMMA, PBT and the similar material to manufacture the diffusion hood of the white light LED source, which may allow the illumination source 11 and the disinfection light source 21 to achieve their own best effects at low cost.

In some embodiments, as shown in FIG. 1, the illumination source 11 comprises a metal core printed circuit board (MCPCB) 14 and an illumination source chip 15 mounted on the MCPCB. Specifically, the illumination source chip 15 may be one or more, and in case of more than one, the illumination source chips are provided on a long strip MCPCB 14 at intervals. The disinfection light source 21 comprises a MCPCB 24 having a UV-protective solder mask and a disinfection light source chip 25 (e.g., UV light source chip) mounted on the MCPCB 24 having a UV-protective solder mask. Specifically, the UV light source chips may be one or more, and in case of more than one, the UV light source chips are provided, at intervals, on a long strip MCPCB 24 having a UV-protective solder mask. In some specific embodiments, the MCPCB 14 and the MCPCB 24 are mounted on the light and disinfection system 100 at an adjustable angle, such that an adjustable angle is formed between the disinfection light source 21 and the illumination source 11, so that the disinfection light source 21 of the disinfection module 20 and the illumination source 11 of the illumination module 10 that are mounted adjacently have a substantially coincident illumination range on an illuminated surface.

Continuing to refer to FIG. 1, in some embodiments, the light and disinfection system 100 also comprises a distance sensor 104, a timing module 105, a detecting sensor 106, a photosensitive sensor 107 and an indicator 108 which are located at the same side of the illumination source 11 and the disinfection light source 21. These components may all be mounted at different positions, rather than the positions defined in the figure. In some other embodiments, the number of the above components may also be greater than one, e.g., two or three.

Figure 2:
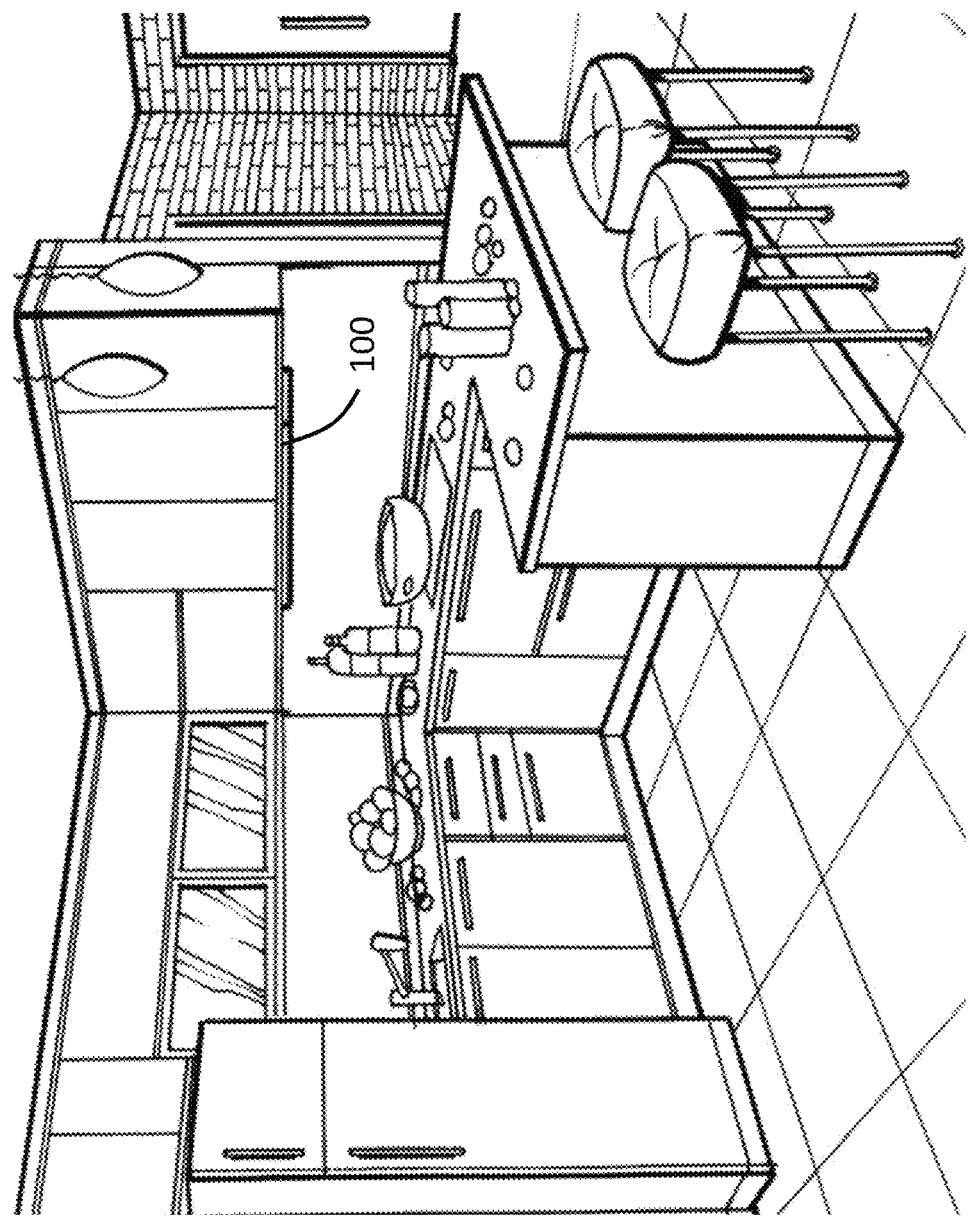
FIG. 2 is a stereogram in which the light and disinfection system shown in FIG. 1 is applied to a lighting scene.

The light and disinfection system of the present application can be used in a kitchen, a bathroom, a home dining room, a home table, an office space, a laundry room, a wardrobe, an office dining room and any other places that need disinfection, sterilization and lighting. In some embodiments, a stereogram of applying the light and disinfection system 100 shown in FIG. 1 to a lighting scene 200 is shown in FIG. 2. In the embodiment, the light and disinfection system 100 is mounted at a bottom of a kitchen cabinet, above a countertop, for lighting the countertop of the kitchen, and performing disinfection and sterilization on the countertop of the kitchen and kitchenware on the countertop.

Figure 3:
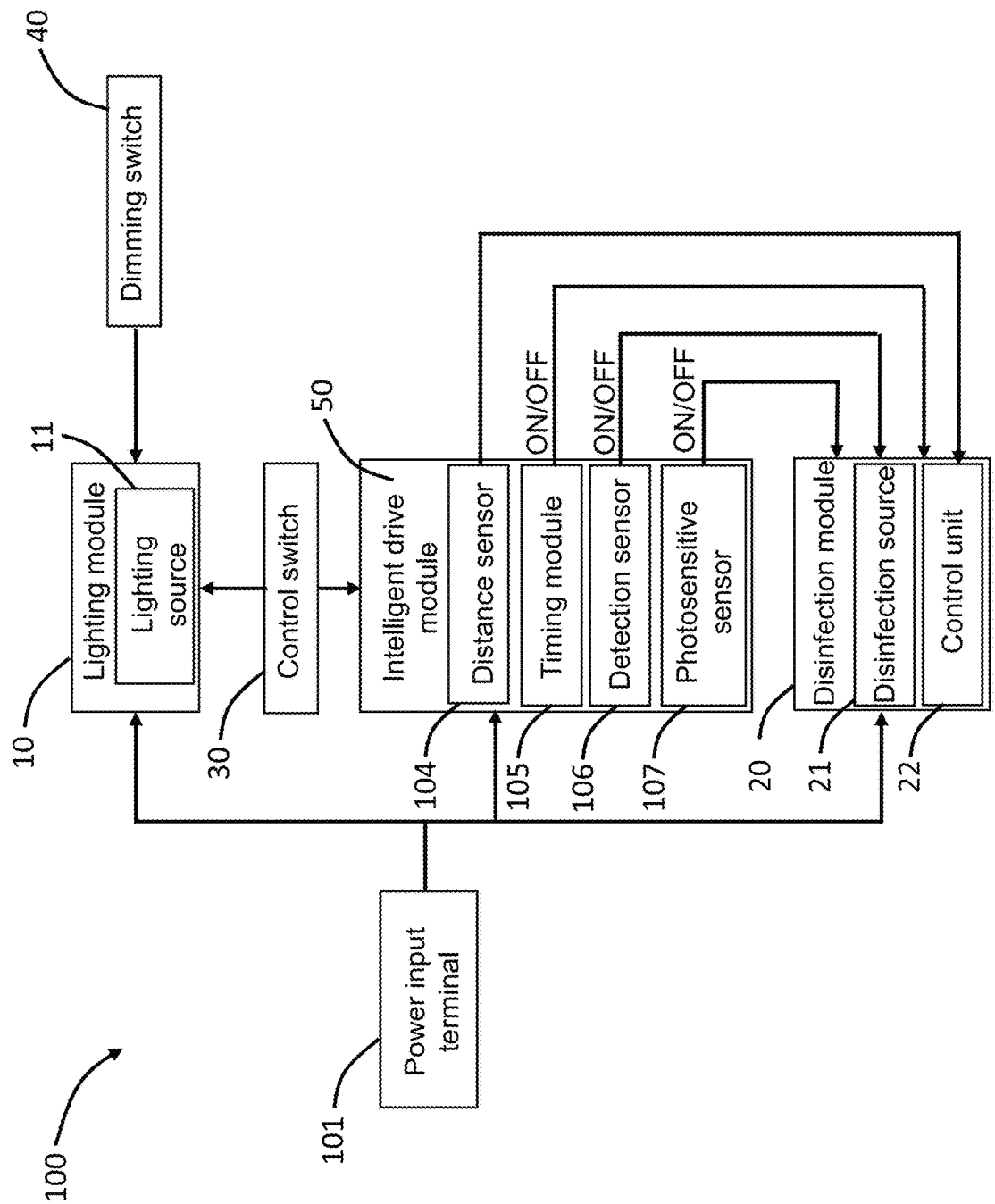
FIG. 3 is a function block diagram of the light and disinfection system shown in FIG. 1.

FIG. 3 is a function block diagram of the light and disinfection system 100 shown in FIG. 1, in which the light and disinfection system 100 supplies power to an illumination module 10, a disinfection module 20 and an intelligent drive module 50 via a power supply input terminal 101. The disinfection module 20 comprises a disinfection light source 21 and a control unit 22, in which the control unit 22 may be built in the disinfection module 20 of FIG. 1. The intelligent drive module 50 comprises a distance sensor 104, a timing module 105, a detecting sensor 106 and a photosensitive sensor 107. The distance sensor 104 is used to detect a distance between the light and disinfection system 100 and the illuminated surface, and the control unit 22 is electrically connected with the distance sensor 104 for receiving a distance signal detected by the distance sensor 104 and controls an irradiation power of the disinfection light source 21 based on the distance, such that an irradiation amount of the illuminated surface accumulated within one disinfection circle is kept at a predetermined value.

The distance sensor 104 can be selected from an ultrasonic ranging sensor, a laser ranging sensor, an infrared ranging sensor, a radar sensor and the like. In some embodiments, the distance sensor 104 can be selected from a sensor such as a laser ranging sensor which measures a distance between two points. With reference to FIG. 2, the laser ranging sensor is used to measure the shortest distance between the laser ranging sensor mounted on the light and disinfection system 100 and the illuminated surface. Depending on the different positions on which the laser ranging sensor is mounted, the measured distance may be a distance between the laser ranging sensor and the kitchen countertop, or may also be a distance between the laser ranging sensor and the kitchenware (e.g., pot). In some embodiments, the distance sensor 104 can be selected from a sensor such as an ultrasonic ranging sensor which measures a distance between a point and a plane. With reference to FIG. 2, the ultrasonic ranging sensor is used to measure a plurality of distances between the ultrasonic ranging sensor mounted on the light and disinfection system 100 and the respective points within a certain range on the illuminated surface which includes both the kitchen countertop and surfaces of all kinds of kitchenware on the countertop. The control unit 22 may select the shortest distance between the ultrasonic ranging sensor and the illuminated surface, or may also select the maximum distance between the ultrasonic ranging sensor and the illuminated surface, or may alternatively select an average distance between the ultrasonic ranging sensor and the illuminated surface, as the basis for controlling the irradiation power of the disinfection light source 21.

In some embodiments, as shown in FIGS. 1 and 2, the light and disinfection system 100 may be arranged above the illuminated surface (e.g., kitchen countertop), within a preset threshold range from the illuminated surface. When the distance between the light and disinfection system 100 and the illuminated surface which is detected by the distance sensor 104 is within the preset threshold range, the control unit 22 controls the irradiation power of the disinfection light source 21 based on the distance such that duration of one disinfection circle is kept at a preset time. In other words, when the distance is within the preset threshold range, the irradiation power can be adjusted within the power range of the disinfection light source 21, such that the irradiation amount of the illuminated surface accumulated within a fixed time of disinfection and sterilization is kept at a predetermined value each time. In some specific embodiments, the preset threshold range is 0.5-2 meters, the preset time is about 7-9 hours, and the predetermined value is about 8.5-9.5 J/m2. In some specific embodiments, the preset time is about 8 hours, and the predetermined value is about 9 J/m2.

In some embodiments, when the distance between the light and disinfection system 100 and the illuminated surface which is detected by the distance sensor 104 is greater than a maximum of the preset threshold range, the control unit 22 adjusts the irradiation power of the disinfection light source 21 to a maximum. At this time, the duration of one disinfection circle is prolonged to be greater than the preset time, thus ensuring that the irradiation amount of the illuminated surface accumulated within one disinfection circle is kept at a predetermined value. When the distance between the light and disinfection system 100 and the illuminated surface which is detected by the distance sensor 104 is less than a minimum of the preset threshold range, the control unit 22 adjusts the irradiation power of the disinfection light source 21 to a minimum. At this time, the duration of one disinfection circle is shortened to be less than the preset time, thus ensuring that the irradiation amount of the illuminated surface accumulated within one disinfection circle is kept at the predetermined value.

Continuing to refer to FIG. 3, in some embodiments, the light and disinfection system 100 comprises a control switch 30 which is coupled to the illumination source 11 of the illumination module 10 and the timing module 105 of the intelligent drive module 50 respectively, for controlling the illumination source 11 and the timing module 105 to be turned on or turned off. In some specific embodiments, the control switch 30 can be a three-step mechanical switch, which will turn on the illumination source 11 and turn off the timing module when in the first step; which will turn off the illumination source 11 and turn on the timing module 105, thus turning on the disinfection light source 21 connected to the timing module 105, when in the second step; which will turn off both the illumination source 11 and the timing module 105 when in the third step.

In order to ensure that the user would not be irradiated by UV light, in some embodiments, the intelligent drive module 50 further comprises a detecting sensor 106 and/or a photosensitive sensor 107 coupled to the disinfection module 20 respectively. Note that the detecting sensor may be a human pyroelectric infrared sensor (PIR), an ultrasonic sensor, a microwave sensor and the like, for detecting whether anybody is nearby when the disinfection light source 21 is turned on. If it is detected that someone is nearby, the disinfection light source 21 will temporarily be turned off; until it is detected that the person is no longer in the detected region of the sensor, the disinfection light source 21 will be turned on again. The photosensitive sensor 107 is used as follows: when the disinfection light source 21 is turned on at night, if the photosensitive sensor 107 detects light that exceeds a preset threshold, it indicates that someone conducts activities with light on, then the disinfection light source 21 will temporarily be turned off; until the photosensitive sensor 107 detects light that does not exceed the preset threshold, then the disinfection light source 21 will be turned on again.

In some embodiments, the intelligent drive module 50 further comprises a timing module 105 coupled to the disinfection module 20. When the illuminated surface needs to be disinfected and sterilized, the control switch 30 turns on the timing module 105, thereby turning on the disinfection light source 21. When the disinfection light source 21 is turned on, the timing is started simultaneously, and when one disinfection circle ends, the timing is stopped and the disinfection light source 21 is turned off, so as to ensure that the effect of disinfection and sterilization achieves an expected standard. In some specific embodiments, the timing module 105 performs timing by counting down. For example, the control switch 30 turns on the timing module 105, and the timing module 105 counts down from 8 hours while the disinfection light source 21 is turned on; when the countdown becomes 0, the disinfection light source 21 will be turned off, and one disinfection circle is finished. When the detecting sensor 106 and the photosensitive sensor 107 detect that someone is active nearby, the timing module 105 stops the timing and temporarily turns off the disinfection light source 21, until no human activity can be detected, then the timing module 105 continues the timing to complete one disinfection circle.

In some embodiments, the timing module 105 further comprises a function of automatically turning on the disinfection light source 21 regularly in a fixed circle. For example, on each Monday morning, at 10 o'clock, the disinfection light source 21 is turned on and the timing is started, disinfecting and sterilizing for one disinfection circle. The time for turning on manually is saved, and on the other hand, the environment is kept clean and hygienic.

In some embodiments, the light and disinfection system 100 further comprises an indicator 108, e.g., an indicator light, for indicating the working status of the disinfection module 20. If the disinfection module is working, the indicator light is on; when the disinfection module is turned off, the indicator light is off; and when the disinfection module is turned off temporarily, the indicator light is flickering.

In some embodiments, as shown in FIG. 3, the light and disinfection system 100 further comprises a dimmer switch 40 coupled to the illumination source 11 of the illumination module 10, for adjusting brightness of the illumination source 11. The dimmer switch 40 can comprise one of three-step dimming, five-step dimming, stepless dimming and the similar dimming manners.

Figure 4:
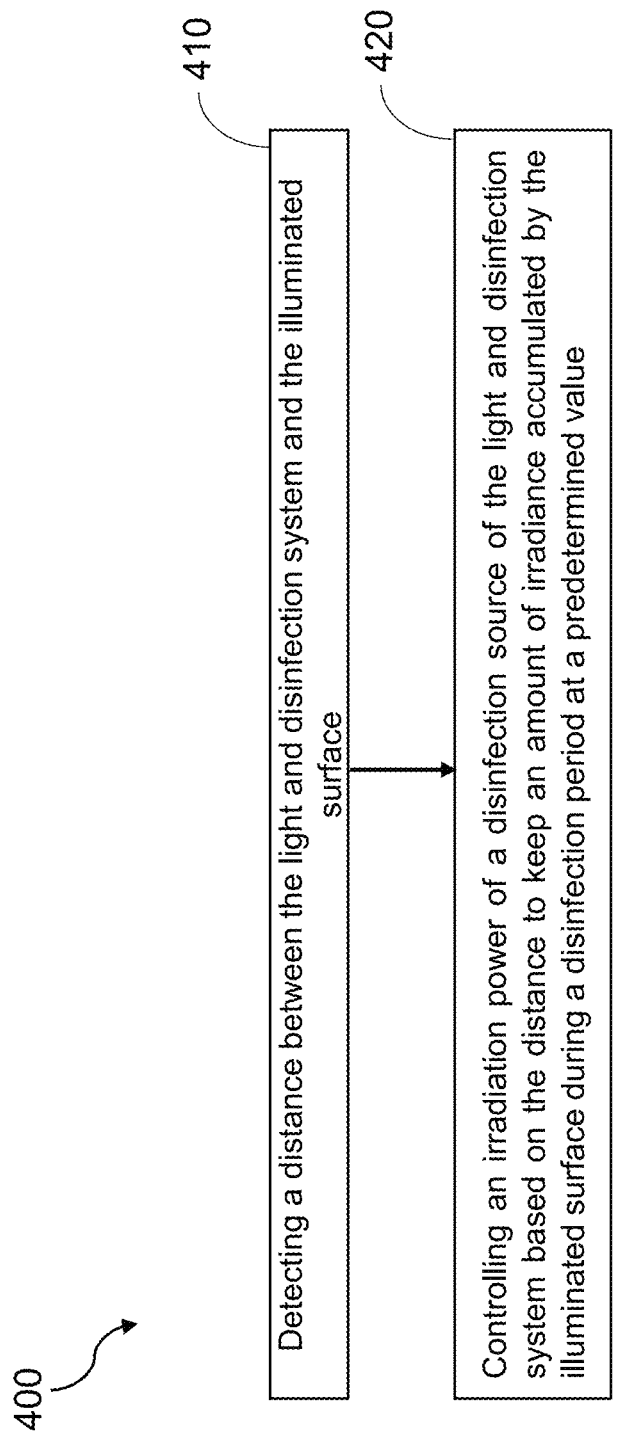
FIG. 4 is a flow chart of a method for disinfecting and sterilizing an illuminated surface by the light and disinfection system according to one embodiment of the present application.

FIG. 4 is a flow chart of a method for disinfecting and sterilizing an illuminated surface by the light and disinfection system according to one embodiment of the present application. With reference to FIG. 1, the method 400 comprises:

Step 410: detecting a distance between the light and disinfection system 100 and the illuminated surface; and Step 420: controlling an irradiation power of the disinfection light source 21 in the light and disinfection system 100 based on the distance, such that an irradiation amount of the illuminated surface accumulated within one disinfection circle is kept at a predetermined value.

In some embodiments, a relationship between the irradiation power P of the disinfection light source 21 and the distance D between the light and disinfection system 100 and the illuminated surface is as shown in the following Equation (1):

$$P = a * D^b \quad (1)$$

wherein a and b are constants, with their values chosen depending on the size and shape of the light and disinfection system 100.

In some specific embodiments, taking a disinfection lamp on the bottom of a kitchen cabinet of 24 inches as an example, the relationship between the irradiation power P of the disinfection light source 21 and the distance D between the light and disinfection system 100 and the illuminated surface is as shown in the following Equation (2):

$$P = 0.01083 * D^{1.719} \quad (2)$$

The light and disinfection system disclosed in the present application may perform a function of lighting when lighting is needed, and perform a function of disinfection and sterilization when people leave, and may adaptively adjust the irradiation power of the disinfection light source based on the distance between the disinfection light source and the surface to be disinfected, such that the irradiation amount accumulated on the surface to be disinfected within each circle of disinfection and sterilization is kept at a predetermined value, so as to ensure efficiency and quality of disinfection and sterilization, thus providing a clean and hygienic place for family and working environment.

Although the present invention has been set forth in details in combination with specific embodiments, the person skilled in the art shall be understood that many modifications and variations may be made to the present invention. Therefore, it should be recognized that the intention of the claims is to cover all these modifications and variations within the real concept and range of the present invention.

What is claimed is:

1. A system for disinfecting an illuminated surface, the system comprising:
    an illumination module, including an illumination source comprising a metal core printed circuit board (MCPCB) and configured to emit non-disinfecting light;
    a distance sensor for detecting a distance between the system and a surface illuminated by the illumination source;
    a disinfection module, including a disinfection light source different from the illumination source comprising a MCPCB and configured to emit disinfecting light;
    wherein the MCPCB of the illumination source comprises a long strip MCPCB and illumination light source elements provided thereon at intervals, wherein the MCPCB of the disinfection light source comprises a long strip MCPCB and disinfection light source elements provided thereon at intervals, and wherein the MCPCB of the illumination source and the MCPCB of the disinfection light source are mounted adjacently to each other on the system and configured such that an adjustable angle is formed between the disinfection light source and the illumination source, the adjustable angle being configured so that light emitted by the disinfection light source and light emitted by the illumination source have a substantially coincident illumination range on the illuminated surface;
    a timing module comprising an automatic timer and being coupled to the disinfection light source for controlling a timing in which the disinfection light source is turned on and off; and
    a control unit configured to receive the distance detected by the distance sensor and control an irradiation power of the disinfection light source based on the distance and the timing, via the automatic timer, such that an irradiation amount of the illuminated surface within one disinfection cycle is kept at a predetermined value.

2. The system according to claim 1, wherein when the one disinfection cycle ends, the timing is stopped and the disinfection light source is turned off, such that the irradiation amount of the illuminated surface accumulated within the one disinfection cycle is kept at the predetermined value.

3. The system according to claim 1, wherein when the distance detected by the distance sensor is within a preset threshold range, the irradiation power of the disinfection light source is controlled based on the distance such that time of the one disinfection cycle is kept at a preset time.

4. The system according to claim 3, wherein the predetermined value is about 8.5-9.5 $J/m^2$, the preset time is about 7-9 hours, and the preset threshold range of the distance is about 0.5-2 meters.

5. The system according to claim 3, wherein when the distance detected by the distance sensor is greater than a maximum of the preset threshold range, the irradiation power of the disinfection light source is adjusted to a maximum, and the time of the one disinfection cycle is greater than the preset time; and wherein when the distance detected by the distance sensor is less than a minimum of the preset threshold range, the irradiation power of the disinfection light source is adjusted to a minimum, and the time of the one disinfection cycle is less than the preset time.

6. The system according to claim 1, wherein the disinfection light source comprises a UV light source including a long-wavelength UV light source having a wavelength ranging from 280 nm to 380 nm.

7. The system according to claim 1, further comprising a dimmer switch coupled to the illumination source for adjusting brightness of the illumination source, wherein the dimmer switch comprises three-step dimming, five-step dimming or stepless dimming.

8. The system according to claim 1, further comprising a detecting sensor or photosensitive sensor mounted on the system, wherein the disinfection light source will be turned off when at least one of the detecting sensor detects that someone is nearby and the photosensitive sensor detects light that exceeds a preset threshold, wherein the detecting sensor comprises a human pyroelectric infrared sensor.

9. The system according to claim 1, wherein the illumination source is configured to emit white light.

10. The system according to claim 9, wherein the disinfection light source is configured to emit UV light.

11. The system according to claim 1, wherein the illumination light source elements comprise illumination light source chips, and wherein the disinfection light source elements comprise illumination light source chips.

* * * * *